United States Patent [19]

Miyamoto

[11] Patent Number: 5,307,161
[45] Date of Patent: Apr. 26, 1994

[54] BIOLOGICAL SAMPLE OBSERVATION SYSTEM USING A SOLID STATE IMAGING DEVICE

[75] Inventor: Shigeyuki Miyamoto, Tokyo, Japan

[73] Assignee: NEC Corporation, Japan

[21] Appl. No.: 866,008

[22] Filed: Apr. 9, 1992

[30] Foreign Application Priority Data

Apr. 12, 1991 [JP] Japan .................. 3-106471

[51] Int. Cl.$^5$ ............................................. H04N 7/18
[52] U.S. Cl. .............................. 348/79; 358/483
[58] Field of Search ............ 358/93, 101, 106, 107, 358/209, 213.11, 225, 229, 482, 483; 382/6; H04N 7/18

[56] References Cited

U.S. PATENT DOCUMENTS

| | | | |
|---|---|---|---|
| 4,499,384 | 2/1985 | Segawa | 358/213.11 |
| 4,626,906 | 12/1986 | Ensor | 358/229 |
| 4,648,074 | 3/1987 | Pollachek |  |
| 4,777,525 | 10/1988 | Preston | 358/93 |
| 4,816,921 | 3/1989 | Akiyama | 358/494 |
| 4,977,313 | 12/1990 | Nagata | 358/482 |
| 5,142,381 | 8/1992 | Kitamura | 358/482 |
| 5,144,458 | 9/1992 | Adachi | 358/213.13 |

FOREIGN PATENT DOCUMENTS 2-208541 8/1990 Japan .

*Primary Examiner*—Tommy P. Chin
*Assistant Examiner*—Bryan S. Tung
*Attorney, Agent, or Firm*—Laff, Whitesel, Conte, Saret

[57] ABSTRACT

A biological sample observation system and method of using a solid-state image sensor element and a holding member, wherein the holding member holds an observation target sample on an upper portion of a light-receiving portion of the solid-state area image sensor element, at a predetermined distance therefrom, and without an optical lens system between the holding member and the image sensor element.

2 Claims, 2 Drawing Sheets

BIOLOGICAL SAMPLE OBSERVATION SYSTEM USING A SOLID STATE IMAGING DEVICE

BACKGROUND OF THE INVENTION

The present invention relates to an apparatus and system for observing a biological sample, and a method therefor.

With the advent of the CCD (charge coupled device), solid-state area image sensor elements have been developed greatly and the characteristics of the solid-state area image sensor elements have considerably improved. Although a solid-state area image sensor element is slightly inferior to a conventional camera tube in terms of resolution, it requires no optical system for forming an image. In addition, the function of photoelectric conversion of a large number of pixels, storage function, and charge read-out function of the solid-state area image sensor element are integrated into an LSI as a solid-state area image sensor device. Therefore, the solid-state area image sensor element is superior to the camera tube in terms of ease in handling, prevention of sticking caused by intense light and of image distortion, and the like. Owing to such advantages, camera tubes have recently been replaced with solid-state area image sensor elements in the field of broadcasting and the like.

Observation of minute biological samples such as cultured cells is mainly performed by a transmission type microscope. Especially for observation of a sample dipped in a liquid such as a culture medium, an inverted microscope having an objective lens arranged below the sample is used. When a microscopic image is recorded, a camera or a video camera mounted on the microscope is used. In addition, especially in the observation of a cultured cell, if the temperature, humidity, and carbon dioxide concentration of the sample must be kept constant, a heat insulating unit, a humidifier, a carbonic acid gas supply unit, and the like are mounted on the sample table of the microscope.

An example of observation of a biological sample by means of a solid-state area image sensor element is disclosed in Japanese Patent Laid-Open No. 2-208541. The disclosed apparatus is designed to detect an immunologic agglutination reaction. In the apparatus, a light-emitting diode is mounted on an agglutination reaction inspection plate, and a light-shielding mask, a condenser lens, and a one-dimensional CCD sensor are arranged below the plate in this order.

A microscope is an optical system including several lenses, prisms, mirrors, and the like. The size of this instrument including optical paths for forming images is considerably large. The size of the instrument is further increased if it includes a video camera required for recording images, and units for keeping the environment of a sample constant, e.g., a heat insulating unit, a humidifier, and a carbonic acid gas supply unit.

Furthermore, since a microscope is a high-precision instrument, it demands careful handling. Therefore, once, for example, the optical axis is shifted, special skills are needed to adjust the optical axis.

Moreover, in general, the heat insulating unit, the humidifier, the carbonic acid gas supply unit, and the like mounted on the sample table of the microscope easily cause variations in conditions such as a variation in temperature as compared with an incubator for performing normal cell cultivation. Since it is difficult to reproduce the same environment as that of the incubator on the sample table, accurate observation is difficult to perform.

In a conventional biological sample observation apparatus using a solid-state area image sensor element, since an optical system including several lenses is arranged between a sample and the image sensor element, problems similar to those in the microscope are posed, i.e., the size of the apparatus is increased, careful handling and adjustment for forming images are demanded, and the like.

SUMMARY OF THE INVENTION

It is an object of the present invention to provide a biological sample observation apparatus and system, which have simple structures and can be easily operated, and a method therefor.

It is another object of the present invention to provide a biological sample observation apparatus and system, which can maintain a proper sample environment, and a method therefor.

It is still another object of the present invention to provide a biological sample observation apparatus and system, which allow continuous observation of an observation target sample while maintaining the environment of the target sample, and a method therefor.

According to an aspect of the present invention, a biological sample observation apparatus comprises a solid-state area image sensor element and a holding member for holding an observation target sample on an upper portion of a light-receiving portion of the solid-state area image sensor element, at a predetermined distance therefrom, without an optical lens system.

According to another aspect of the present invention, there is provided a biological sample observation system comprising at least one biological sample observation apparatus including a solid-state area image sensor element, and a holding member for holding an observation target sample on an upper portion of a light-receiving portion of the solid-state area image sensor element, at a predetermined distance therefrom, without an optical lens system, driving means for driving the solid-state area image sensor element arranged in the biological sample observation apparatus, and display means for performing data display of a sample image in accordance with an output signal from the solid-state area area image sensor element.

According to still another aspect of the present invention, there is provided a biological sample observation method comprising the steps of holding an observation target sample on an upper portion of a light-receiving portion of a solid-state area image sensor element without an optical lens system, and reading data from the target sample by driving the solid-state image sensor element, and obtaining a sample image by using an output signal from the target sample.

DESCRIPTION OF THE PREFERRED EMBODIMENTS

Embodiments of the present invention will be described below with reference to the accompanying drawings.

Figure 1:
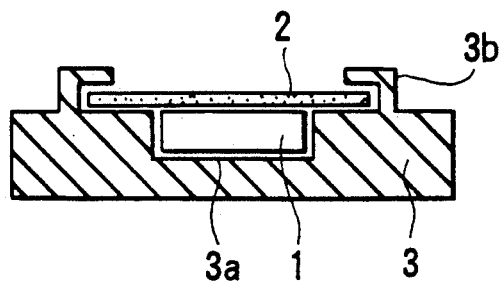
FIG. 1 is a sectional view showing a biological sample observation apparatus according to an embodiment of the present invention.

FIG. 1 is a sectional view showing a biological sample observation apparatus according to an embodiment of the present invention. Referring to FIG. 1, reference numeral 1 denotes a solid-state area image sensor element such as a CCD; 2, an observation target sample; and 3, a holding member having a recess portion 3a for containing the solid-state area image sensor element 1 at an upper central position of the member, and holding arms 3b surrounding the recess portion 3a and designed to hold the sample 2. Each holding arm 3b has an inverted L-shaped cross-section. The sample 2 held by the holding member 3 has an observation target portion located immediately above the light-receiving surface of the solid-state area image sensor element 1 at a predetermined distance therefrom. With this structure, the apparatus requires no optical lens system between the sample and the solid-state area image sensor element, unlike a conventional apparatus. Therefore, the apparatus is greatly simplified.

The distance between the solid-state image pickup element 1 and the sample 2 is preferably set to be 1 cm or less in order to prevent an out-of-focus state of an image. Within this range, a transparent plate can be inserted between the solid-state area image sensor element 1 and the sample 2 to protect the element 1, or a sharp image can be obtained by inserting a filter for limiting all incident light or light having a specific wavelength.

If the apparatus includes a mechanism for moving the holding member 3 with respect to the solid-state area image sensor element 1, it can be suitably applied to observation of a sample larger than the light-receiving surface of the element 1. In addition, by changing the shape of the holding member 3, not only the plate-like sample shown in FIG. 1 but also a sample such as a petri dish containing a culture solution can be observed.

Since the apparatus includes no light source, it can be suitably applied to observation of a sample emitting light with a phosphor marker in a dark place. It is obvious that if only the light-receiving portion of the apparatus is covered to prevent external light from entering the apparatus, observation need not be performed in a darkroom.

Figure 2:
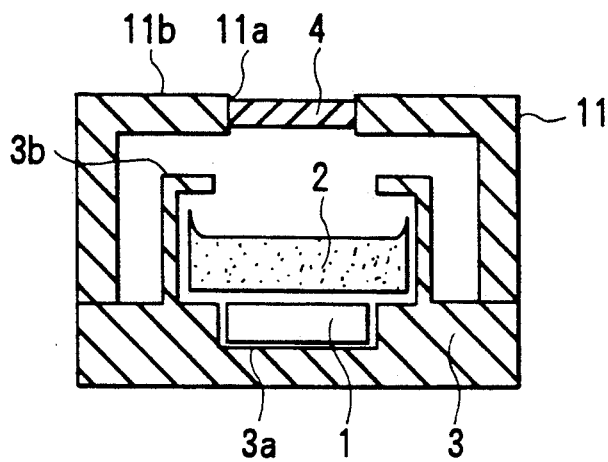
FIG. 2 is a sectional view showing a biological sample observation apparatus according to another embodiment of the present invention.

FIG. 2 is a sectional view showing a biological sample observation apparatus according to another embodiment of the present invention. This apparatus is designed to receive external light to allow observation of a sample which emits no light. In addition to the components of the apparatus shown in FIG. 1, this apparatus includes a cap-like darkroom member 11 having a window 11a on a ceiling portion 11b and placed on the holding member 3 to cover the sample 2, and a filter 4 arranged at the window 11a located above the sample 2 and designed to reduce the amount of external light. Light adjusted by the filter 4 is guided to the light-receiving surface of a solid-state area image sensor element 1.

It is preferable that rays of light having an intensity matching the characteristics of the solid-state area images sensor element 1 and the same traveling direction be radiated on the light-receiving surface of the element 1. In order to satisfy such a condition, as the filter 4, one or a combination of the following components can be used: a filter, a diaphragm, a pinhole, a slit, and a deflection plate, which are designed to reduce the amount of external light or align rays in the same traveling direction, a scattering plate for scattering light, and a color filter for transmitting light having a specific wavelength.

Figure 3:
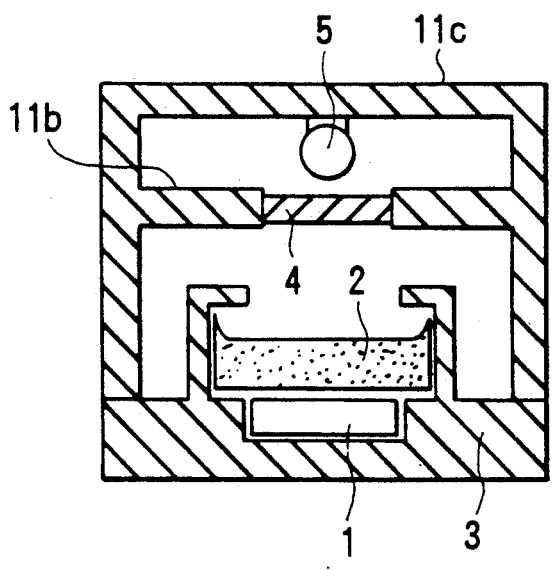
FIG. 3 is a sectional view showing a biological sample observation apparatus according to still another embodiment of the present invention.

FIG. 3 is a sectional view showing a biological sample observation apparatus according to still another embodiment of the present invention. In addition to the components of the apparatus shown in FIG. 2, this apparatus includes a roof portion 11c on a ceiling portion 11b of a darkroom member 11. A light source 5 is arranged on the roof portion 11c above a filter 4. For example, the intensity of light from the light source 5 is adjusted by the filter 4. The resultant light is then incident on the light-receiving surface of a solid-state area image sensor element 1. Since the intensity of light can be easily controlled by changing an applied voltage or the like, a sharper image can be obtained as compared with the apparatus shown in FIG. 2. The apparatus may include a plurality of light sources. As light sources, light bulbs, light-emitting diodes, electroluminescence elements, and the like can be used.

Figure 4:
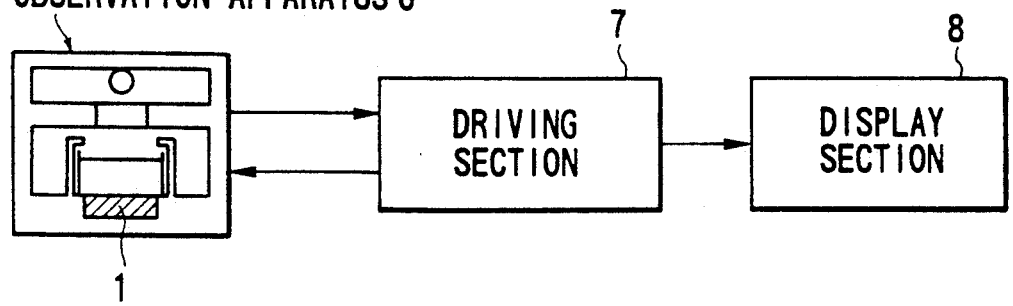
FIG. 4 is a block diagram showing a biological sample observation system according to an embodiment of the present invention.

FIG. 4 shows the arrangement of a biological sample observation system according to an embodiment of the present invention. As a biological sample observation apparatus 6, either an apparatus of the type having no light source, shown in FIGS. 1 and 2, or an apparatus of the type having a light source, shown in FIG. 3, can be used. A solid-state area image sensor element 1 in the biological sample observation apparatus 6 is driven by a driving section 7 to perform a reading operation. Image information from this element 1 is supplied to a display section 8 through the driving section 7. As a result, a sample image is data-displayed. If the display section 8 includes an image recording function and an image digital processing function as well as an image display function, a system suitable for a given purpose of observation can be realized.

In addition, a plurality of biological sample observation apparatuses 6 may be prepared to be selectively connected to the single driving section 7 and the single display section 8 by a switching control scheme. Alternatively, pairs of biological sample observation apparatuses 6 and driving sections 7 may be prepared to be selectively connected to the single display section 8 by a switching control scheme. With such a system, a large number of samples can be observed at once.

Figure 5:
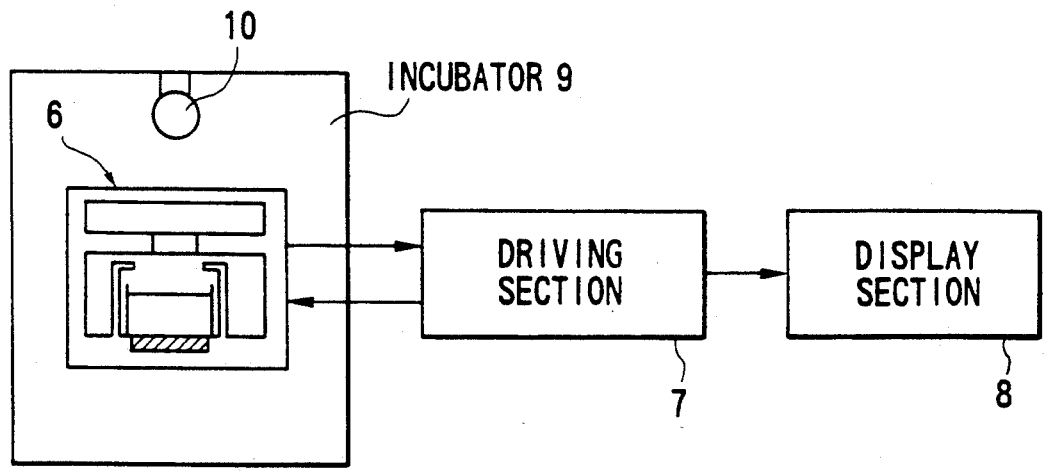
FIG. 5 is a biological sample observation system according to another embodiment of the present invention.

FIG. 5 shows the arrangement of a biological sample observation system according to another embodiment of the present invention. This system is characterized in that only the biological sample observation apparatus 6 in the system shown in FIG. 4 is housed in an incubator 9. The incubator 9 can control the internal temperature, humidity, and gas concentration, e.g., carbon dioxide concentration to keep them constant. Since a sample 2 is placed in the incubator together with the biological sample observation apparatus 6, observation of the biological sample can be performed in a well-controlled environment. This system is especially suitable for continuous observation of cells or bacteria.

If a light source 10 is arranged in the incubator 9 to control the amount of light, since the light source 5 need not be arranged in the biological sample observation apparatus 6, the apparatus can be simplified accordingly. This system is especially suitable for a case wherein a plurality of samples are observed by different biological sample observation apparatuses, because the same observation conditions can be set for the respective apparatuses.

Examples of observation based on a biological sample observation method of the present invention will be described next.

EXAMPLE 1

Analysis of an electromigration gel was performed on the basis of the biological sample observation method of the present invention. Electromigration of a sample was performed by using Phast Gel Gradient 10-15 available from Pharmacia Fine Chemicals, Inc. After a gel film was dyed, the film was placed on a biological sample observation apparatus of the present invention to observe an electromigration pattern. Digital image processing of the obtained image was performed by a personal computer to detect the position and density of a band, thereby identifying a protein in the sample.

This analysis method requires no laser, unlike a method using a densitometer, and hence allows a reduction in size of the apparatus. In addition, since scanning of laser light is not performed, the time required for measurement can be shortened.

EXAMPLE 2

An immunologic agglutination reaction was detected on the basis of the biological sample observation method of the present invention. A transparent petri dish was placed on a biological sample observation apparatus of the present invention. The petri dish contained 2 ml of 9-mmol phosphate buffer (pH 7.4) containing 3.5 mg of latex (particle diameter: 1.08 $\mu$m; Sekisui Chemical Co., Ltd.) sensitized with hCG antibody (Medics Biochemica Inc.). The petri dish and the apparatus were placed in an incubator. After the sample containing hCG was added to the petri dish, observation of the petri dish was started. The hCG concentration in the sample was determined by observing the number of latex particles, which agglomerated due to an immunologic reaction and allowed to settle, over time.

EXAMPLE 3

Observation of cultured cells was performed on the basis of the biological sample observation method of the present invention. 2 ml of an aqueous solution containing 0.03% of collagen and 0.2% of acetic acid was put in a polystyrene petri dish available from Falcon Inc., and the petri dish was left to stand for 10 min to adsorb the collagen. 1,000,000 rat hepotocytes together with a culture medium were placed on the petri dish which was washed with water. The petri dish was fixed in a biological sample observation apparatus of the present invention. The petri dish and the apparatus were placed in an incubator at a temperature of 37° C., a humidity of 90%, and a carbon dioxide concentration of 5%. Cultivation was continued for 18 hours, and changes in the cells were observed.

As has been described above, in each biological sample observation apparatus of the present invention, since an observation target sample is directly held on the upper portion of the light-receiving portion of a solid-state area image sensor element, an optical system including lenses and the like, which is required in the prior art such as a microscope, can be omitted. Therefore, the size of the apparatus can be reduced. In addition, if light having a proper intensity can be ensured, or a sample with a phosphor marker is used, no light source is required. This further simplifies the apparatus. Furthermore, since the apparatus has a simple structure and uses no fragile members such as vacuum tubes and lenses, it is resistant to careless handling, i.e., impact and the like. Since adjustment for forming an image, e.g., focusing, is not required, observation is facilitated.

If the apparatus includes a light source for radiating light on the light-receiving portion of an element through a sample, the intensity of light can be easily controlled by changing an applied voltage or the like, thus obtaining a sharper image.

In addition, the biological sample observation apparatus in which a sample is held on the upper portion of the solid-state area image sensor element can be formed into a biological sample observation system suitable for a given purpose of observation by connecting a driving section for driving the element to a display section for displaying a sample image in accordance with an output signal from the element. Especially, if a plurality of biological sample observation apparatuses are prepared to be selectively connected to the driving section and the display section by a switching control scheme, a large number of samples can be observed at once. Furthermore, in this system, the size of the biological sample observation apparatus is small, and the apparatus is free from the problem of lens distortion at a high temperature, the problem of blurring of an optical lens system at a high humidity, and the like. Therefore, this apparatus can be used in combination with a control chamber in which the temperature, humidity, gas concentration, and the like are controlled. For example, the apparatus can be placed in an incubator for performing normal cell cultivation. That is, the use of the system of the present invention allows continuous observation of a biological sample under proper conditions of temperature, humidity, and gas concentration. The system is especially suitable for continuous observation of cells and bacteria.

Moreover, in this system, a light source is arranged in the control chamber to also control light radiated on a sample. With this arrangement, no light source need be arranged in the biological sample observation apparatus. If a plurality of apparatuses are arranged in the control chamber, the same observation conditions can be set for the respective apparatuses.

What is claimed is:

1. A biological sample observation system comprising:
   at least one biological sample observation apparatus including a solid-state area image sensor element, or converting an optical image of an observation target sample to image signals for electronically displaying said optical image,
   a control chamber for housing said biological sample observation apparatus and controlling at least one of an internal temperature, humidity, and gas concentration, a holding member for holding an observation target sample on an upper portion of a light-receiving portion of said solid-state area image sensor element, at a predetermined distance therefrom, without an optical lens system between the holding member and the image sensor element, said solid-state area image sensor element and said holding member being supported in a non-movable relationship with respect to each other;

driving means for driving said solid-state area image sensor element in said biological sample observation apparatus to perform a reading operation; and display means for displaying an image of said observation target sample in accordance with an output signal from said solid-state area image sensor element.

2. A system according to claim 6, wherein said control chamber further controls light to be radiated on the target sample.

* * * * *